United States Patent [19]
Sundman et al.

[11] Patent Number: 5,689,446
[45] Date of Patent: Nov. 18, 1997

[54] FOOT CONTOUR DIGITIZER

[75] Inventors: Arjen Sundman, Santa Cruz, Calif.;
Brian F. Smithgall, Bozeman, Mont.;
Tony G. Tadin, Woodside, Calif.

[73] Assignee: Amfit, Inc., Santa Clara, Calif.

[21] Appl. No.: 552,539

[22] Filed: Nov. 3, 1995

[51] Int. Cl.⁶ ................................................. G06K 9/00
[52] U.S. Cl. .................... 364/560; 364/401 R; 364/403;
364/413.13; 364/413.22; 364/550; 364/560;
33/4; 33/5; 33/6; 33/3 A; 33/3 B; 33/3 C;
33/3 R; 356/374; 356/376; 356/380; 356/386
[58] Field of Search .................... 364/560, 401 R,
364/403, 550, 413.13, 413.22; 33/504,
505, 3 R, 4–6, 3 A–3 C; 382/126, 321;
356/374, 376, 380, 386

[56] References Cited

U.S. PATENT DOCUMENTS

| 4,454,618 | 6/1984 | Curchod | 12/1 R |
|---|---|---|---|
| 4,604,807 | 8/1986 | Bock et al. | 33/3 C |
| 4,745,290 | 5/1988 | Frankel et al. | 250/560 |
| 4,858,621 | 8/1989 | Franks | 128/779 |
| 4,876,758 | 10/1989 | Rolloff et al. | 12/142 |
| 5,025,476 | 6/1991 | Gould et al. | 382/2 |
| 5,102,223 | 4/1992 | Uesugi et al. | 356/376 |
| 5,128,880 | 7/1992 | White | 364/550 |
| 5,195,030 | 3/1993 | White | 364/401 |
| 5,206,804 | 4/1993 | Thies et al. | 364/401 R |
| 5,216,594 | 6/1993 | White et al. | 364/560 |
| 5,231,723 | 8/1993 | White et al. | 12/133 R |
| 5,237,520 | 8/1993 | White | 364/560 |
| 5,361,133 | 11/1994 | Brown et al. | 356/376 |
| 5,539,677 | 7/1996 | Smith | 364/560 |

Primary Examiner—Emanuel T. Voeltz
Assistant Examiner—Hien Vo
Attorney, Agent, or Firm—Ohlandt, Greeley, Ruggiero & Perle

[57] ABSTRACT

Apparatus for determining a contour of the underside of a person's foot includes an array of gauge pins supported by a first support structure and disposed in spaced relation for independent, guided movement along their longitudinal axes. An inflatable diaphragm elevates the gauge pins into extended positions until they contact the underside of the foot. A camera, forward of the gauge pin array, is pointed towards the gauge pin array. An initial reference image is captured of the gauge pins in their retracted position. The person's foot is then placed on the first support structure and the gauge pins are elevated (by means of the diaphragm). The gauge pins are locked in place; the foot is removed and an image of the conforming gauge pin array is acquired by the camera, using ambient light. The image is sent to a processor which analyzes the image and compares it to the reference image to determine the new location of the tops of the gauge pins. The apparatus also allows measurement of the top surface of the foot, including the heel. This is accomplished via an optical scanning system which makes use of a light bar projector in conjunction with a camera to first scan the top of the gauge element array to acquire a reference image for each light bar position. Then, a person's foot is placed on the gauge pin array and the entire foot is scanned. The resulting images enable the processor to determine the contour of the upper portion of the foot.

28 Claims, 7 Drawing Sheets

FOOT CONTOUR DIGITIZER

FIELD OF THE INVENTION

This invention relates to apparatus for making measurements of a foot and, more particularly, to a method and apparatus for digitizing the foot measurements so as to enable generation of contour representations of all surfaces of the foot.

BACKGROUND OF THE INVENTION

Measuring the shape of a foot, especially the underside, is not a straightforward task. The human foot undergoes many changes in shape during gait, including expanding and lengthening. It has hard and soft areas that react differently when weight is applied.

A number of prior art references include teachings regarding automatic and semi-automatic systems for measurement of foot size. For instance, see U.S. Pat. Nos. 5,128,880; 5,195,030; 5,206,804; 5,216,594; 5,231,723; and 5,237,520, all to White or White et al. White teaches the placement of a foot upon a transparent reference surface and scanning the underside of the foot. The scanning action enables a differentiation of the relative distances of portions of the foot from the reference surface and enables the effects off different foot pressures to be visualized.

U.S. Pat. No. 4,454,618 entitled "System and Method for Forming Custom-Made Shoe Insert," to Curchod, assigned to the same Assignee as this Application, describes a system for forming a custom-made, resilient insert for a person's shoe which conforms to the under-surface of the person's foot. The Curchod invention includes a plate with an array of axially movable gauge pins and an inflatable diaphragm which yieldingly urges the gauge pins upwards to an extended position. While the gauge pins are in their lowered position, a person places a foot upon them and they are then elevated into contact with the undersurface of the foot. The gauge pins are locked in their conforming positions and a tracing head is moved across their upper surfaces. The tracing head action simultaneously moves a cutting head assembly which cuts a blank of foam rubber or other suitable material to conform to the contour defined by the upper surfaces of the gauge pins.

An improvement to the structure disclosed by Curchod is disclosed in European Patent Specification 0 284 922 B1, entitled "Improved Apparatus, System and Method for Forming Custom-Made Shoe Inserts," Rolloff et al assigned to the same Assignee as this Application. The Rolloff, et al. invention employs a similar gauge pin array as is employed in the Curchod structure. Each gauge pin, however, includes a pair of permanent magnets disposed in opposed relationship at a predetermined intermediate location along the pin's length. Once the gauge pins have been conformed to a person's foot, a sensing mechanism is moved relative to the gauge pin array under control of a stepper motor. The sensing mechanism comprises a plurality of Hall effect sensors and is stepped along the gauge pin array. The resulting scan action produces signals indicative of the position of each pin. The signals are then processed by a computer to provide a stored digital representation of the contour of the under-surface of the foot which depressed the pins.

The structures described by Curchod and Rolloff, et al. exhibit a number of advantages. First, by varying the air pressure in the inflatable diaphragm which controls the elevation of the gauge pins, an effect can be created of providing additional foot support by the deflection of soft areas of the foot through interaction with the pins. Next, an orthotic appliance, having pre-positioned holes which mate with the gauge pins, can be placed under the foot and mated with the gauge pin array to test the orthotic's therapeutic effect. The gauge pins then capture the modified foot position/anatomy. Lastly, the operator is enabled to record the contour of the underside of the foot with any amount of weight on the subject foot.

While the aforedescribed structures provide an accurate contour of the underside of a foot, the mechanical apparatus for moving and supporting the Hall-effect sensors, the required magnets and motor drive structures add a level of undesired expense to the apparatus.

Accordingly, it is an object to this invention to provide a foot contour digitizer exhibiting a simplified mechanical structure.

It is a further object of this invention to provide a foot contour digitizer which enables a contour to be obtained of not only the under-side of a foot, but also contours of upper portions of the foot, including the heel.

SUMMARY OF THE INVENTION

Apparatus for determining a contour of the underside of a person's foot includes an array of gauge pins supported by a first support structure and disposed in spaced relation for independent, guided movement along their longitudinal axes. The exposed top end of the gauge pins may have a contrasting shade or unique color to allow for easy identification. An inflatable diaphragm elevates the gauge pins into extended positions until they contact the underside of the foot. A mechanism allows the gauge pins to be locked in their respective elevated positions.

A camera, forward of the gauge pin array, is pointed towards the gauge pin array. The gauge pin array's first support structure includes indexing marks indicating where the extents are of the gauge pins. An initial image is captured of the gauge pins in their retracted position (i.e., a reference image).

The person's foot is then placed on the first support structure and the gauge pins are elevated (by means of the diaphragm). The gauge pins are locked in place; the foot is removed from the gauge pin array; and an image of the conforming gauge pin array is acquired by the camera.

The image is converted to a digital form. If the camera uses film, the photograph or slide is optically scanned and sent to the processor. In the case of a video camera, a frame grabber is used. In the case of a digital camera, the data is sent directly to the processor. The processor then analyzes the image and compares it to the reference image to determine the new location of the tops of the gauge pins. Using triangulation, the heights of the gauge pins is determined.

The invention also allows measurement of the top surface of the foot, including the heel. This is accomplished via an optical scanning system which makes use of a light bar projector in conjunction with a camera to view the top of the gauge pin array.

Initially (prior to a foot being placed on the gauge pin array), a series of images is recorded by the camera and sent to a processor. The light bar projector is initially set to project the light bar at one end of the gauge pin array. An image is acquired and sent to a processor. The light bar is swept a known amount and another image is acquired. The process is repeated until the entire gauge pin array has been scanned. This series of images constitute the reference images for each light bar position.

To sample the upper surface of the foot, the light bar projector is initially set to project the light bar at one end of the gauge pin array. An image is acquired and sent to the processor. The light bar is swept a known amount and another image is acquired. The process is repeated until the entire foot has been scanned.

At the rear of the foot, the heel is out of view. This blind spot is measured by means of a mirror. The light bar is reflected off the mirror and against the heel. The resulting image is reflected and captured by the camera. The image processing is nearly identical to the directly measured area.

DETAILED DESCRIPTION OF THE INVENTION

Figure 1:
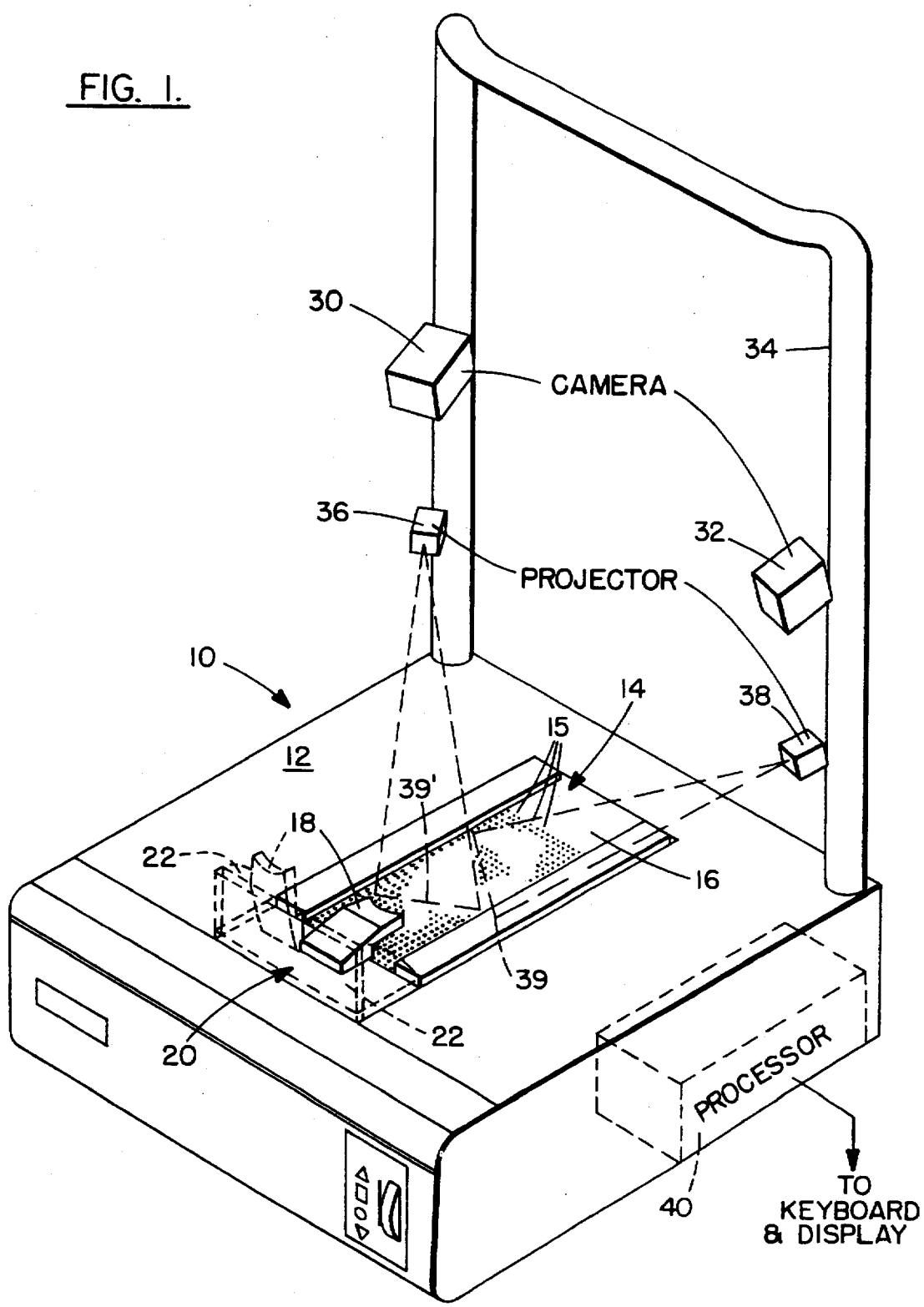
FIG. 1 is an isometric view of a structure incorporating the invention hereof.
Figure 2:
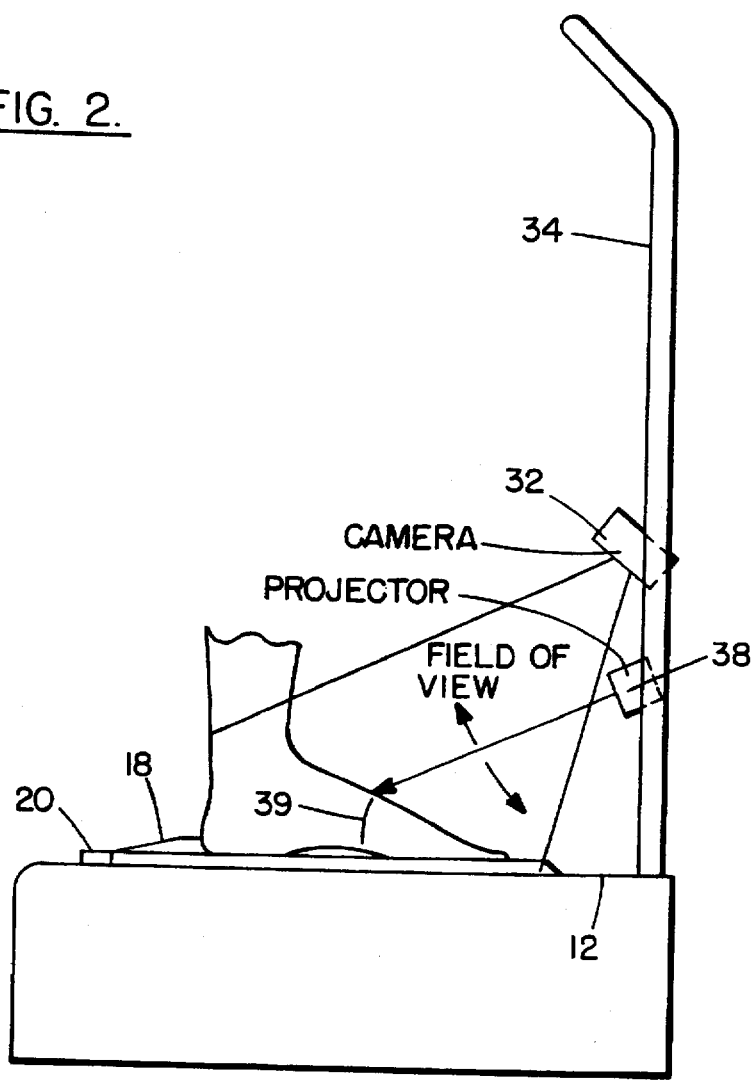
FIG. 2 is a side view of the structure of FIG. 1.
Figure 3:
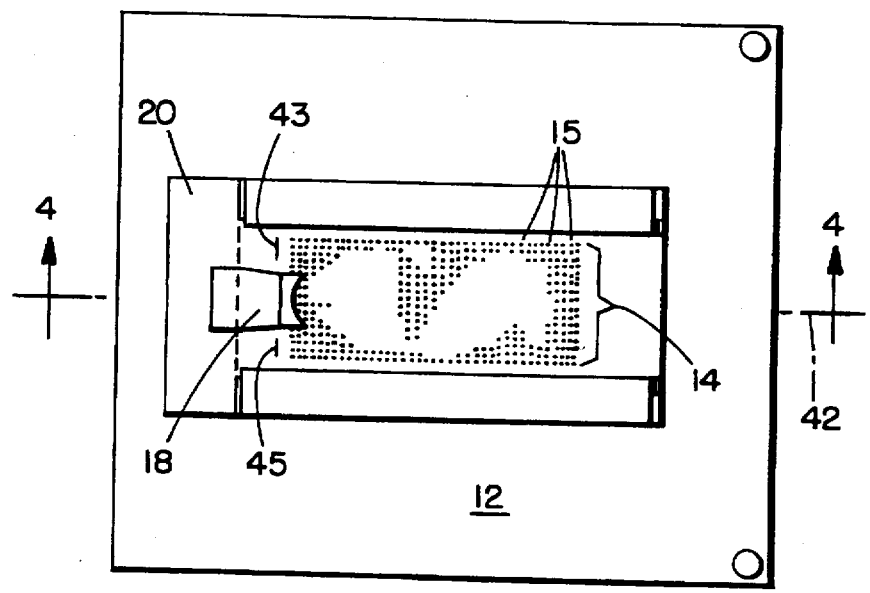
FIG. 3 is a top view of the gauge pin surface.

Referring to FIGS. 1–3, a foot contour digitizer 10 is shown in accordance with a preferred embodiment of the invention. Foot contour digitizer 10 includes a support plate 12 in which is positioned an array 14 of gauge pins 15 which is used to form an impression of the undersurface of a person's foot. In FIG. 1, gauge pins 15 are shown in their "home" position where they are fully withdrawn into a foot support plate 16. A heel guide 18 is attached, at its rearmost position, to a plate 20 which is rotatable between a vertical position and a horizontal position. In the horizontal position, heel guide 18 is positioned to receive a person's heel and to properly position the foot in relation to array 14 of guide pins 15. Plate 20, in the vertical position, exposes a mirror surface 22 which is used during subsequent imaging of a person's heel.

Figure 4A:
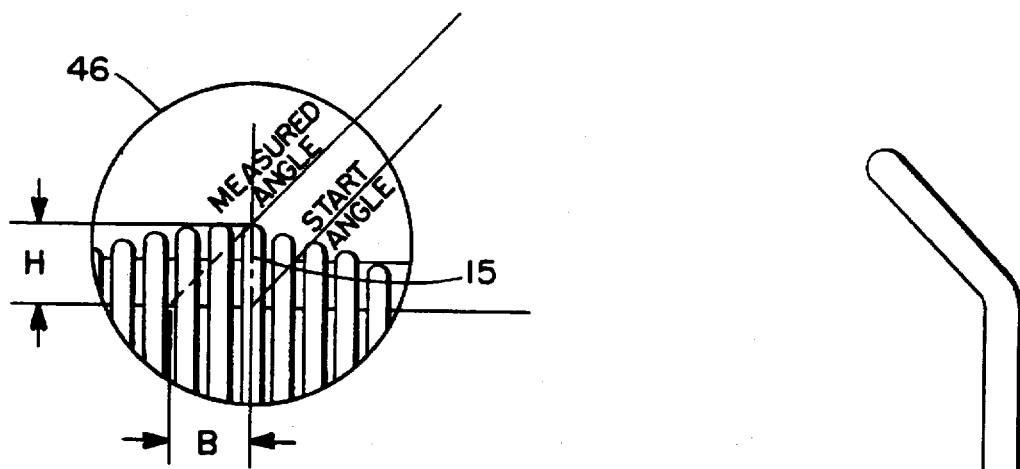
FIG. 4a is a magnified portion of the view of FIG. 4
Figure 4:
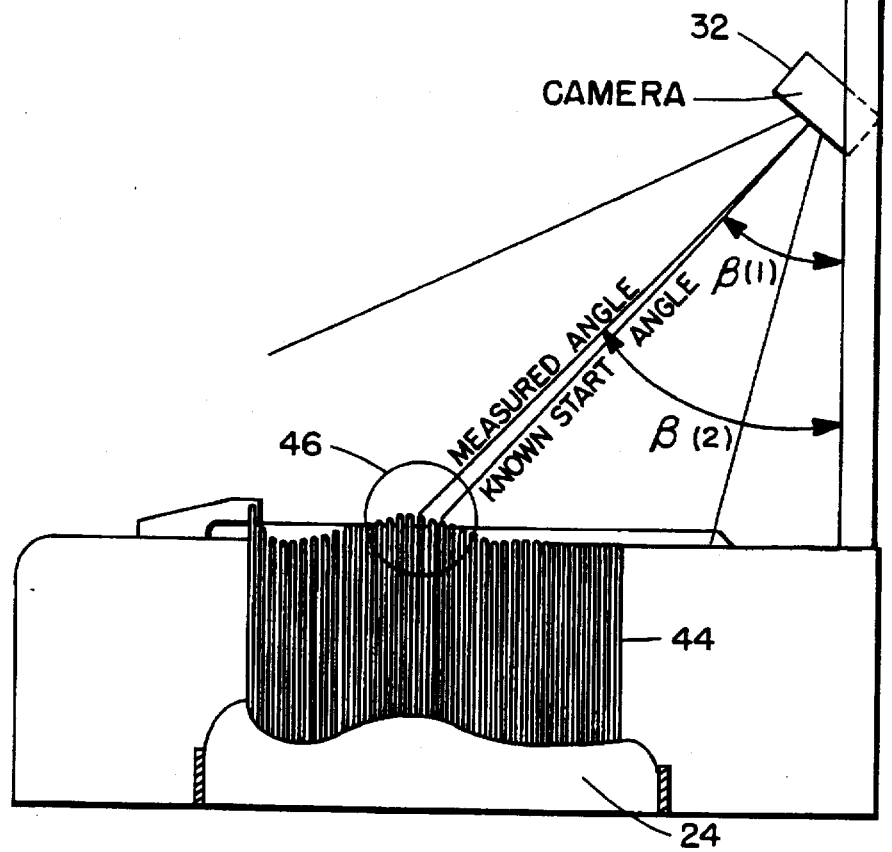
FIG. 4 is a schematic sectional view taken along line 4—4 in FIG. 3 and illustrates the geometry which is employed to calculate the height of extension of each gauge pin.

Each gauge pin 15 in array 14 is supported by an inflatable diaphragm 24 (see FIG. 4). A person's foot is placed upon array 14. Diaphragm 24 is inflated and provides a resilient elevating force which urges gauge pins 15 into contact with the under surface of said person's foot. The pins are then locked into position for subsequent imaging. The structure of the inflatable diaphragm/locking mechanism is essentially similar to that shown in U.S. Pat. No. 4,454,618 and European Patent Specification 0 284 922 B1, and the disclosures thereof are incorporated herein by reference.

To enable imaging of array 14 of gauge pins 15 and the uppermost surfaces of a person's foot, a pair of cameras 30 and 32 are positioned on a frame 34. Further, a pair of light projectors 36 and 38 are also similarly positioned on frame 34. The support structures which extend from frame 34 to cameras 30, 32 and light projectors 36 and 38 are not shown, to avoid over complication of the view.

Each of cameras 30, 32 has a field of view which includes the entire surface of array 14 and, further, the upper portions of a person's foot when the foot is positioned on array 14 of gauge pins 15 (see FIG. 2). Each of projectors 38 projects a bar of light 39. Each of light projectors 36, 38 may be comprised of (1) a laser/mirror/scan mechanism, (2) a laser light source with a lens for achieving scanned light bar 39, or (3) an incandescent light source that is projected through a slot to achieve scanned light bar 39. In all cases, light sources 36, 38 (see FIG. 2) are controlled so that projected light bars 39, 39' are orthogonal to the center-line of the light source from which the light bar is projected.

The images of swept light bar 39 are captured in frames by cameras 30, 32 and are stored in memory in a processor 40. Processor 40 provides output signals which synchronize the operations of cameras 30, 32 and control the sweep operations of projectors 36, 38. A keyboard and display are connected to processor 40 but are not shown in the drawings.

FIG. 3 is a plan view of array 14 of gauge pins 15 and shows it to be a rectangular array of rows of gauge pins 15 that are symmetrically arranged along an axis 42. A pair of reference marks 43 and 45 are used to enable initial positioning of light bar 39 and to further enable cameras 30 and 32 to properly reference the position of array 14. FIG. 4 is a section taken along line 4—4 in FIG. 3 and illustrates a column 44 of gauge pins 15 after they have been raised upward into contact with the underside of a person's foot and have been locked in place.

As will hereafter be understood, the invention employs two imaging techniques to acquire surface data regarding the contour of array 14 and a foot positioned on array 14. Swept light bar(s) 39 enables acquisition of contour data by cameras 30 and 32 of a foot positioned on array 14. By contrast, ambient light images of array 14 are used to determine the elevation of gauge pins 15 and, thus, the contour of array 14.

Prior to placement of a person's foot on array 14, all gauge pins 15 are placed in their home or downmost position. At such time a reference calibration image is acquired. This may be a one time or a periodic event to allow for accommodation of variations in the mechanical relationships of the various lights, cameras, and gauge elements. The reference calibration image is initially acquired by capturing an image of array 14 through use of one of cameras 30 or 32 (using ambient light). That reference calibration image is then used during analysis of gauge pins 15, after they have acquired the contour of a person's foot, to enable the heights of the various gauge pins to be determined.

Further reference calibration images are acquired by each projector 36, 38 scanning light bar 39 down the length of array 14. These scan bar reference images are used when the upper surfaces of the person's foot are scanned and provide the datum which enables elevations of the foot to be determined. To acquire these reference calibration images, a light projector (e.g., projector 38) scans light bar 39 down the length of array 14 of fully retracted gauge pins 15. Camera 32 captures an image of reflections of light bar 39 off the top surface of the array 14.

When imaging gauge pin array 14, it is preferred to use a single camera 30 or 32. By analysis of the position of the reflections from each gauge pin 15 in the image frame, processor 40 is enabled to establish a known start angle $\beta(1)$ for each gauge pin 15 in its home position. Thereafter, when gauge pins 15 take the form of the contour of a person's foot, a further analysis of an image of each gauge pin 15 enables a determination of a measured angle $\beta(2)$ for each pin.

Angles β(1) and β(2), in conjunction with known mechanical relationships of foot contour digitizer 10, further enable the amount of linear extension of each gauge pin 15 from foot support plate 16 to be determined.

Figure 5:
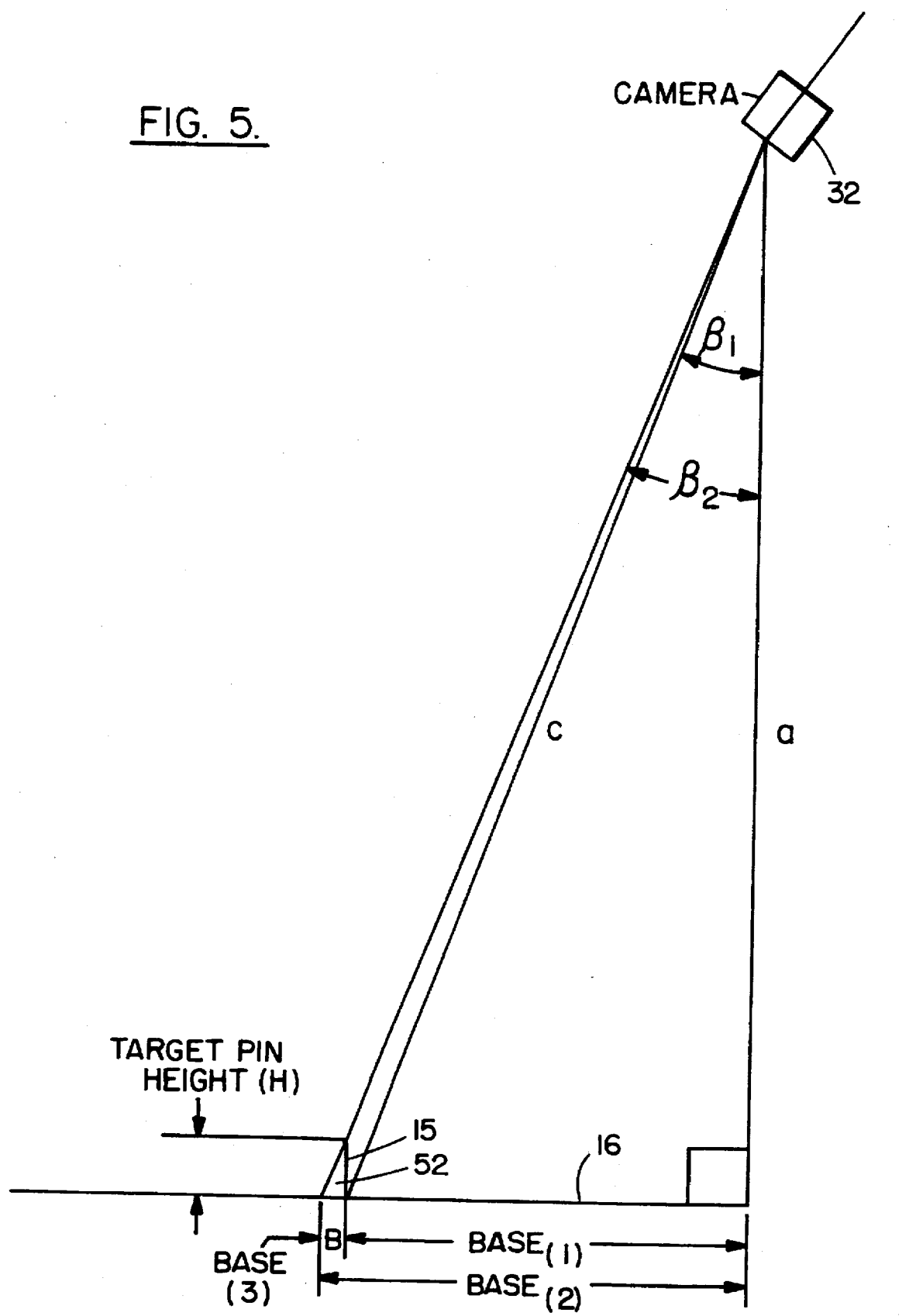
FIG. 5 is a simplified view of the geometry of FIG. 4, enabling a better understanding thereof.

A circular area 46 of FIG. 4 is shown magnified in FIG. 4a wherein a gauge pin 15 is shown in an extended position. The height H of gauge pin 50 is determined by a geometric comparison of start angle β(1) and measured angle β(2) to derive a triangle having a base B. In FIG. 5, the specific geometry employed by processor 40 to determine H is illustrated. Certain positional measurements are known from mechanical relationships of foot contour digitizer 10, to wit: the length of vertical dimension "a" from plate 16 to camera 32 and the length of "base(1)" dimension along plate 16. From the reference calibration image (when gauge pin 15 is in its home position), the angle β(1) is determined and the length of hypotenuse "c" is calculated, knowing the dimension of "base(1)". After gauge pin 15 conforms to a person's foot, a subsequent image analysis occurs. At such time, the tip of gauge pin 15 will have moved upwardly, thereby causing the light reflected therefrom to move within the field of view of camera 32.

The change in position of reflected light from the tip of gauge pin 15 enables angle β(2) to be found. This is achieved by first determining the length of "base(2)". The dimension of "base(2)" may be determined by comparing the position of the light reflection after gauge pin 15 is in an extended position, with the position of the light reflection when gauge pin 15 is in its home position. A proportion is derived which enables the direct derivation of the length of "base(2)" from the known dimension of "base(1)".

Thereafter, to find height H, the following calculations are performed:

base(3)=base(2)−base(1)

tangent β(2)=a/base(2)

height (H)=base(3)*cotangent β(2)

As can be seen from the above relations, the derivation of the value H for gauge pin 15 is readily found from known mechanical relationships, results of the reference calibration scan of array 14 when all of gauge pins 15 are in their home position, and a subsequent scan of array 14 after gauge pins 15 have been moved into contact with a user's foot. One skilled in the art will realize that the initial scan of gauge pins 15 could also occur when all gauge pins 15 are in their fully extended position. The geometry required to determine H for each gauge pin 15 would then require modification, such modification being readily apparent to one skilled in the art.

Figure 6:
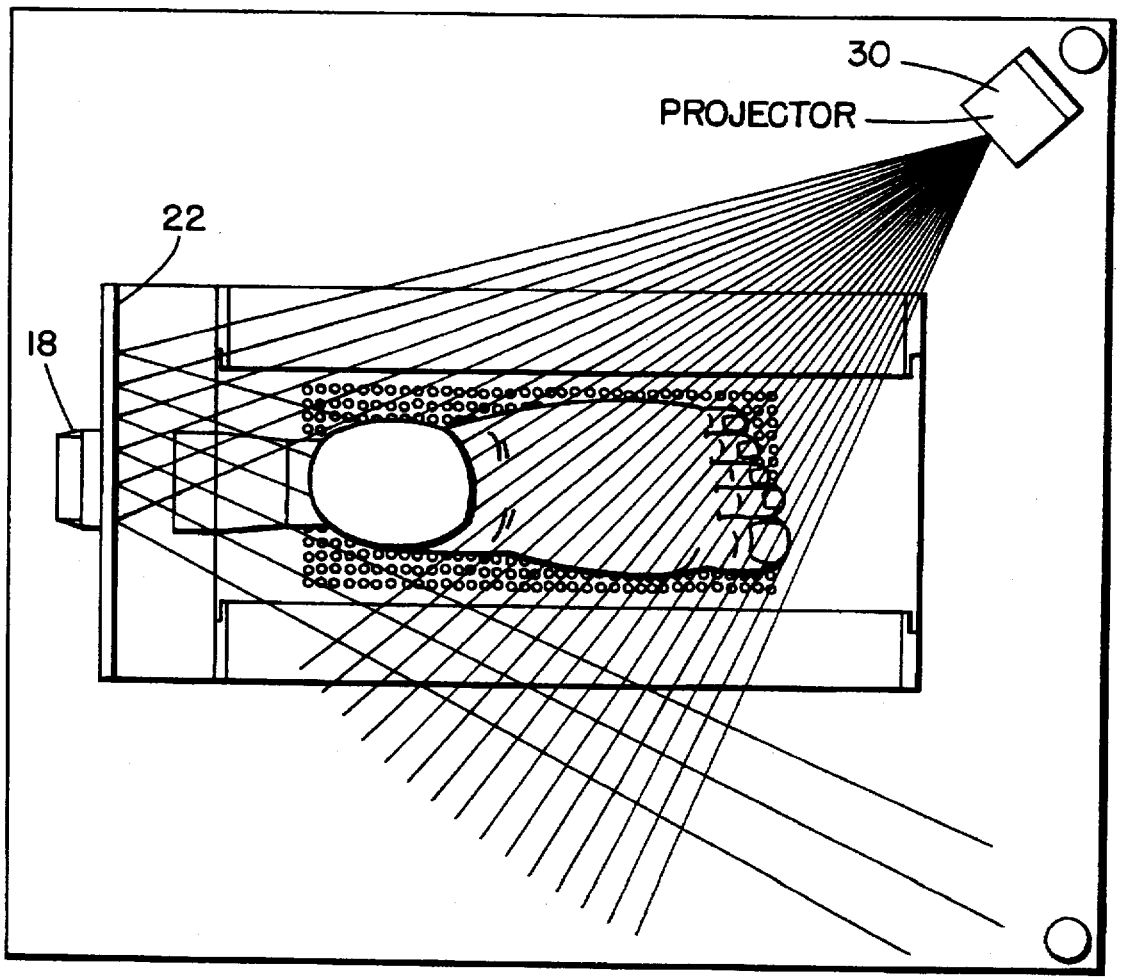
FIG. 6 illustrates the operation of the invention when imaging the left side of a person's foot.
Figure 7:
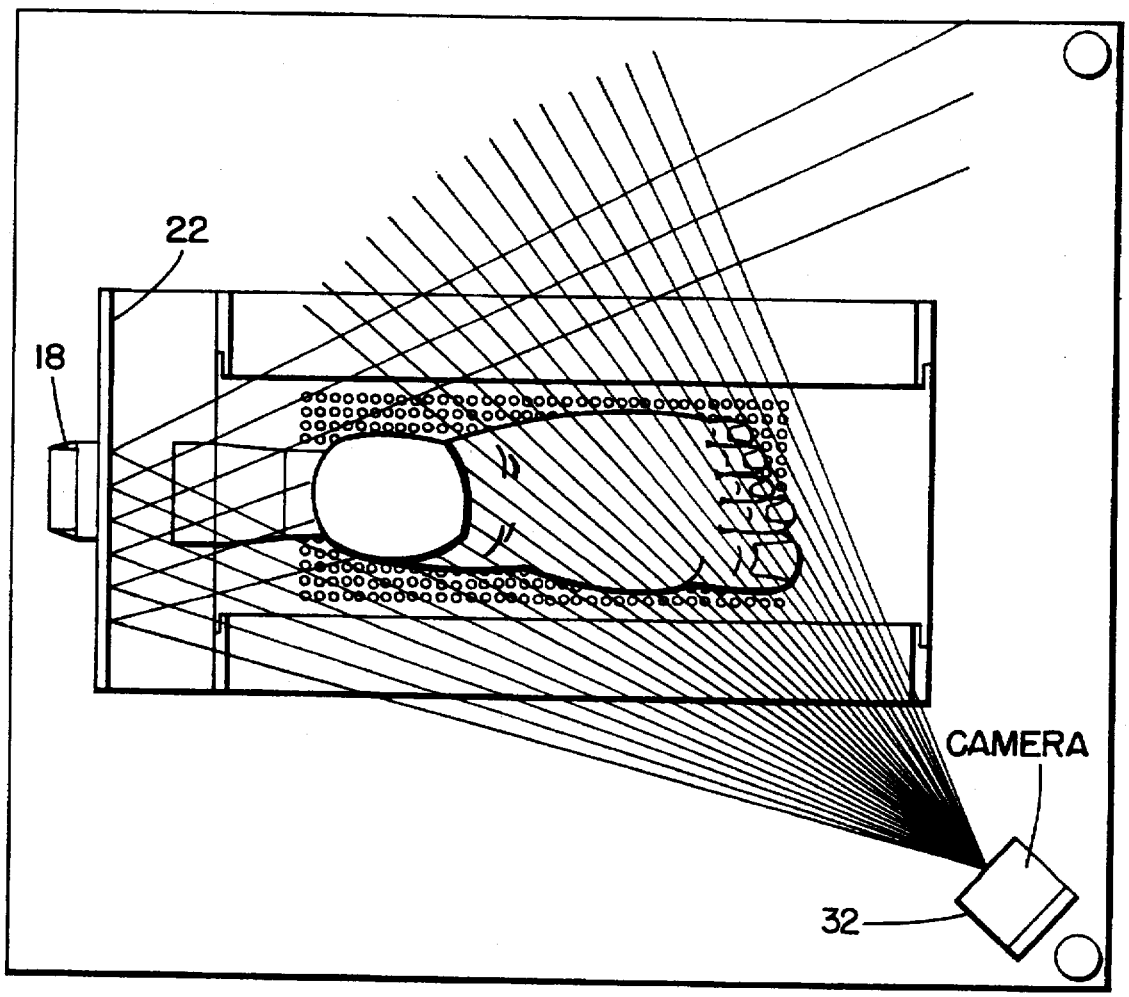
FIG. 7 illustrates the operation of the invention when imaging the right side of a person's foot.

As shown in FIGS. 6 and 7, the system of FIG. 1 enables a digitization of upper portion of a person's foot. In specific, the projection of a light bar 39 from projector 36 enables camera 30 to image a reflection of light bar 39 from the upper left side of a person's foot. In similar fashion, camera 32, upon a projection of a light bar 39 from projector 38, is enabled to view a reflection thereof from the right side of a person's foot. Using similar geometric calculations to those described above and a previously acquired reference calibration image, a series of values can be determined which define the contour of the uppermost portions of a person's foot.

Figure 8:
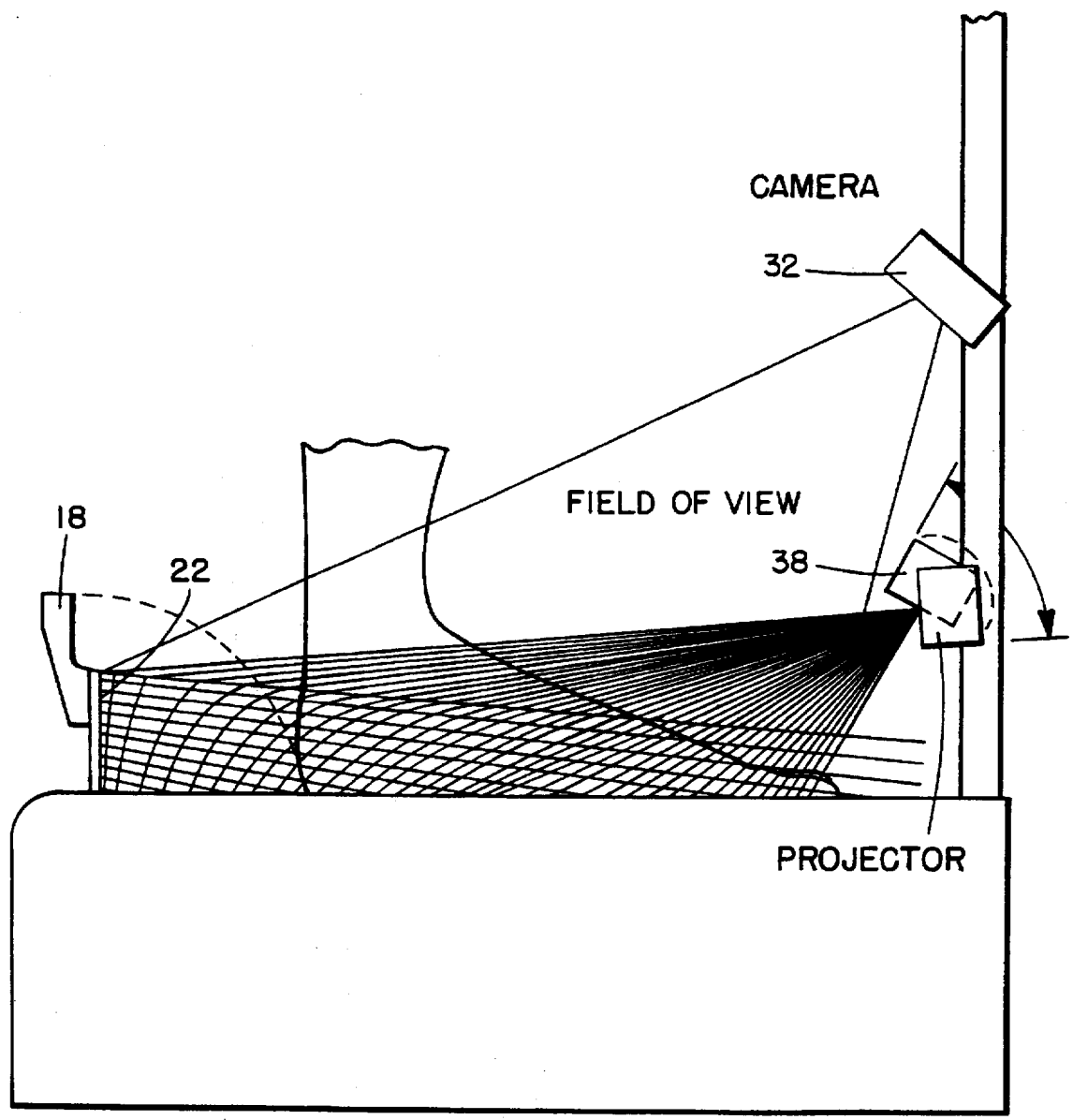
FIG. 8 illustrates the operation of the invention when imaging the heel portion of a person's foot.

To enable an acquisition of an image of the heel of the person's foot (see FIG. 8), heel guide 18 is rotated upwardly, thereby exposing mirror 22 to the scanned light bar from a light projector. Using the same imaging procedure, the rear contour of the person's heel can be obtained in accordance with reflections viewed from mirror surface 22. Light bar 39 is reflected by mirror 22 onto the heel of the foot. The resulting image is again reflected in mirror 22 and is captured by the respectively operating camera. Since light projectors 36 and 38 are positioned above the plane of mirror 22, the reflections of light bar 39 are projected both onto the heel and onto array 14. Thus, the previously acquired reference calibration image data can be used to determine the heel's contour.

In operation, when using one video camera, a light bar from a light projector is pointed slightly past one end of the person's foot (say past the toes), and vibrations are allowed to settle out. During a next video field, the camera acquires an image of the light bar and the image is analyzed during a next video image time. Acquisition proceeds continuously and the data is analyzed during alternate images. For example, when a left image is being acquired, the prior right image is being analyzed.

A series of images is thus acquired and analyzed, the number of which is determined by the resolution required and the time available for imaging. There are 60 fields per second (in NTSC countries) and 30 frames per second. Depending on the resolution required, this allows for 30 or 60 measurements per second. If dual cameras are employed, analysis is alternated between the two cameras and requires that light projectors 36 and 38 be alternately turned on at 60 Hz rate. The number of measurements is 30 right and 30 left which enables 60–90 images to be acquired in a 2–3 second time frame.

A more precise description of the operation of the system, under control of processor 40, is as follows:

1. The right and left light bars are positioned at a home position which entails rotating light projectors 36 and 38 to a known start angle.
2. Either the left or right light bar projector is turned on. Assume the left light bar projector 36 is turned on.
3. Record image from left camera 30 and analyze the image to find light bar in the image. Triangulate deviations from straight line and store elevation data.
4. Turn off left light bar projector 36 and increment left light line a known number of degrees.
5. Turn on right light bar projector 38.
6. Record image in right camera 32 and analyze as in step 3.
7. Turn off right light bar projector 38 and increment right light bar projector 38 a known number of degrees.
8. Go to step 2 and repeat steps 2–8 until the scan is completed.

To synchronize the above actions with a video scan action, each projector move, imaging and analysis action occurs in 1/60th of a second.

Once the contour data is obtained, the length, width and volume of the person's foot can be calculated. Thereafter, any portion of the foot image can be displayed. If a database of foot size data is maintained, the acquired contour data can be compared and any portion of the contour which exceeds a norm for a particular size can be emphasized on the display by a different color or grey level.

Further, the image of array 14 acquired by a camera, with light bar 39 off, enables the exact contour of gauge pins 15 to be available for use during a subsequent machining of an orthotic (e.g. shaped insole) by a digitally controlled shaping mechanism. The memory within processor 40 can also be preloaded with length, width and volume data of shoe sizes. Then, the data acquired as a result of the above described scan actions can be compared with the pre-stored shoe size data to arrive at an appropriate shoe for the user's foot.

Further, an orthotic shape (with holes to match the gauge pins) can be placed under the foot during imaging for the purpose of modifying the foot's at rest position. Then, the volume data acquired for the foot and orthotic shape is used to assess a proper shoe configuration from a data base of stored configurations. The aforesaid data can also be used to enable a subsequent re-shaping of the orthotic to accommodate a desired type of footwear.

Foot volume can also be calculated so as to enable a metering of a precise amount of a semi-fluid conformal material into a sole mold. Then, when foot pressure is placed onto the semi-fluid material, overflow is avoided and an optimal conforming sole (after curing) is created.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

We claim:

1. Apparatus for determining a contour of a portion of a person's foot, said apparatus including an array of gauge elements supported by a first support structure and disposed in spaced relation for independent guided movement along longitudinal axes of said gauge elements, from a home position to an extended position, and first control means for urging said gauge elements into extended positions so as to contact said portion of the person's foot, said apparatus further comprising:

camera means for acquiring a reference image of reflections of said gauge elements when said gauge elements are disposed in a reference position, and for further acquiring a contour image of reflections of said gauge elements in extended positions after contact with the person's foot; and control means for receiving said reference image and contour image and calculating therefrom, a digital value indicative of a linear measure of an amount of extension of each said gauge element to enable said determination of said contour.

2. The apparatus as recited in claim 1, wherein said reference position of said gauge elements is when said gauge elements are in their respective home position.

3. The apparatus as recited in claim 1, wherein each said gauge element includes an uppermost tip that reflects light differently from remaining portions of said gauge element, to enable said control means to distinguish reflections from tips of said gauge elements from reflections from other areas of said gauge elements.

4. The apparatus as recited in claim 1, wherein said first support structure includes at least one reference mark to enable said control means to determine a position of said array of gauge elements.

5. The apparatus as recited in claim 1, further comprising:

means for locking said gauge elements in said extended positions after contact with the person's foot.

6. A method for determining a contour of a portion of a person's foot, said method employing apparatus including an array of rows of gauge elements supported by a support structure and disposed in spaced relation for independently guided movement along longitudinal axes, from a home position towards said portion of a person's foot, and control means for urging said gauge elements into extended positions in contact with said portion of the person's foot, said method comprising the steps of:

acquiring a first image of reflections of ambient light from said gauge elements when in a reference position;

elevating said gauge elements to extended positions into contact with the person's foot;

acquiring a second image of reflections of said ambient light from said gauge elements after said person's foot has been removed therefrom;

determining from said first image and second image and known mechanical dimensions of said support means, a digital value indicative of a linear measure of an amount of extension of each said gauge element to enable determination of said contour.

7. The method as recited in claim 6, comprising the further step of:

locking said gauge pins in said elevated positions after said elevating step.

8. The method as recited in claim 6, comprising the further step of:

employing coordinate points of said contour to determine dimensions of a custom contoured insole for said foot.

9. The method as recited in claim 6, wherein said array of gauge elements is planar in shape, and said apparatus includes a first camera, a second camera, a first light projector and a second light projector, said first camera and first light projector positioned to view one side of a foot positioned on said array and said second camera and second light projector positioned to view a second side of a foot positioned on said array, said method comprising the further steps of:

acquiring images from said first camera and second camera of projected light bars across upper surface areas of said person's foot; and determining coordinate points of said upper surface areas of said foot through use of said images.

10. The method as recited in claim 9, comprising the further steps of:

employing said coordinate points to determine dimensions of said foot; and employing said dimensions to find a shoe which matches said dimensions from among stored data defining shoes.

11. The method as recited in claim 9, comprising the further steps of:

employing said coordinate points to determine volume dimensions of said person's foot; and employing said volume dimensions to determine a metered amount of a mold material to be used for placement into a container and about a portion of the person's foot.

12. The method as recited in claim 6, wherein said array of gauge elements is planar in shape, and said apparatus includes a camera and a light projector, said camera and light projector positioned to view a foot positioned on said array, said method comprising the further steps of:

acquiring images from said first camera of a light bar projected by said light projector across upper surface areas of said person's foot; and determining coordinate points of said upper surface areas of said foot through use of said images.

13. Apparatus for determining a contour of a portion of a person's foot, said apparatus including an array of gauge elements supported by a first support structure and disposed in spaced relation for independent guided movement along longitudinal axes of said gauge elements, from a home position to an extended position, and first control means for urging said gauge elements into extended positions so as to contact said portion of the person's foot, said apparatus further comprising:

projection means for projecting a light bar across said array of gauge elements when said gauge elements are disposed in a reference position;

camera means for acquiring images of reflections of said light bar;

means for locking said gauge elements into said extended positions after contact with said portion of the person's foot;

control means coupled to said projection means and said camera means, for operating said projection means to project said light bar along said gauge elements when positioned in said reference position and, further, along a person's foot positioned on said gauge elements, said control means receiving images of reflections of said light bar from said camera means and calculating therefrom, digital values indicative of a contour of said person's foot.

14. The apparatus as recited in claim 13, wherein said reference position of said gauge elements is when said gauge elements are in their respective home position.

15. The apparatus as recited in claim 13, wherein each said gauge element includes an uppermost tip that reflects said light bar differently from remaining portions of said gauge element, to enable said control means to distinguish reflections from tips of said gauge elements from reflections from other areas of said gauge elements.

16. The apparatus as recited in claim 13, wherein said projection means increments said light bar in discrete steps across said array and across said person's foot, and said control means employs images from said camera means which occur at a same discrete step to determine contour values.

17. The apparatus as recited in claim 13, wherein said array of gauge elements is planar in shape to receive a person's foot, said camera means comprising a first camera and a second camera, said projection means comprising a first light projector and a second light projector, said first camera and first light projector positioned to view one side of a foot positioned on said array and said second camera and second light projector positioned to view a second side of a foot positioned on said array, said control means responsive to images from said first camera and second camera to determine coordinate points of upper surface areas of said foot, prior to said foot being removed from said gauge elements.

18. The apparatus as recited in claim 17, further comprising;

mirror means positioned at one end of said array for reflecting said light bar onto a heel area of said foot and for further reflecting an image of said heel area and incident light bar to a camera for production of an image thereof, said image employed by said control means to determine a dimension of said foot.

19. The apparatus as recited in claim 13, wherein said control means employs said digital values to determine dimensions of a shaped insole for said foot.

20. The apparatus as recited in claim 13, wherein said control means employs said digital values to determine a correct shoe size for said foot.

21. The apparatus as recited in claim 13, wherein said control means employs said digital values to determine volume dimensions of said person's foot and employs said volume dimensions to determine a metered amount of a mold material to be placed into a container and about a portion of the person's foot.

22. The apparatus as recited in claim 13, wherein said control means includes a display and employs said digital values to display contours of said foot, said control means further comparing said digital values against stored values in a database and, for any portion of said contours of said foot which varies from a normal range of said stored values, displaying said portion in a distinctive manner from other portions of said foot.

23. The apparatus as recited in claim 13, wherein a shaped insole is emplaced in registration with said gauge pins and prior to placement of said foot thereon, and said light bar is scanned thereover with said foot in place on said shaped insole, said control means employing said digital values to determine volume dimensions of both said person's foot and said shaped insole, for determining a shoe configuration to match said volume dimensions.

24. The apparatus as recited in claim 23, wherein said control means determines changes required to said shaped insole to enable production of a changed, shaped insole which, when combined with said person's foot, matches a chosen shoe.

25. The apparatus as recited in claim 23, wherein said control means determines changes required to said shaped insole to enable production of a changed, shaped insole which matches irregularities in a chosen shoe.

26. The apparatus as recited in claim 13, wherein said control means includes a display which visually demonstrates a fit between a subject's foot, a computer simulated custom insole to be fabricated, and a shoe selected.

27. The apparatus as recited in claim 13, wherein said control means includes a database of available footwear and employs foot data and insole data, to display a likeness of the footwear suitable for the subject's foot.

28. The apparatus as recited in claim 13, wherein said control means includes a database of available footwear, an inventory control system, foot data, and insole data, and displays a likeness of footwear in stock that is suitable for the subject foot.

* * * * *